United States Patent [19]

Weaver et al.

[11] Patent Number: 5,424,092
[45] Date of Patent: Jun. 13, 1995

[54] APPARATUS FOR CYANOACRYLATE FINGERPRINT DEVELOPING AND METHOD OF USE THEREFORE

[75] Inventors: David E. Weaver; Everett J. Clary; Robert J. Shem; George M. Taft, Jr., all of Anchorage, Ak.

[73] Assignee: State of Alaska, Dept. of Public Safety, Anchorage, Ak.

[21] Appl. No.: 285,947

[22] Filed: Aug. 4, 1994

Related U.S. Application Data

[63] Continuation-in-part of Ser. No. 70,772, Jun. 3, 1993, Pat. No. 5,348,759.

[51] Int. Cl.[6] ............................................. H61B 5/117
[52] U.S. Cl. ................................. 427/1; 118/31.5; 118/47; 156/278; 156/293; 156/294; 427/223; 427/230; 427/239; 427/255.6

[58] Field of Search ................. 427/1, 223, 255.6, 239, 427/230; 118/31.5, 47; 427/223, 255-256, 239, 230; 156/278, 293, 294

[56] References Cited

FOREIGN PATENT DOCUMENTS 001616 3/1988 WIPO ................................. 427/1

Primary Examiner—Janyce Bell
Attorney, Agent, or Firm—Michael J. Tavella

[57] ABSTRACT

A housing for developing latent fingerprints is formed by positioning a thermally stable porous support material in a hollow tubular member and impregnating the support material with a liquid cyanoacrylate which is allowed to cure. The housing can be placed on an end of a portable heating device having sufficient heat to vaporize the cyanoacrylate and project the vapors against an object to be tested for latent fingerprints.

13 Claims, 1 Drawing Sheet

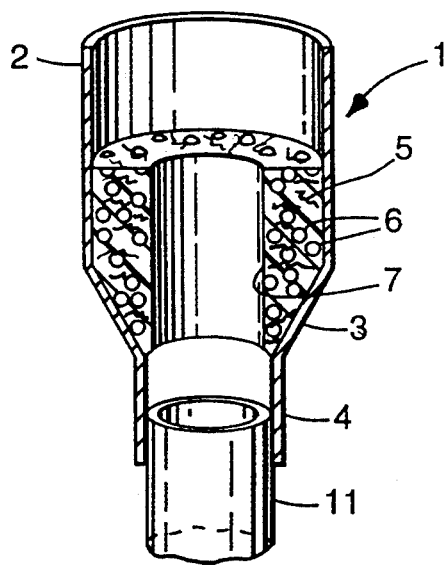
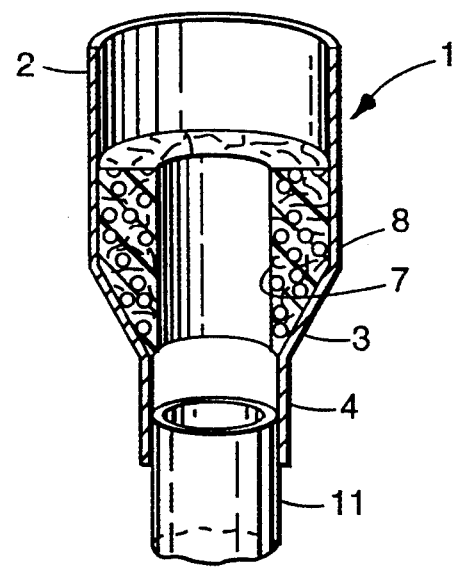
FIG.1  FIG.2
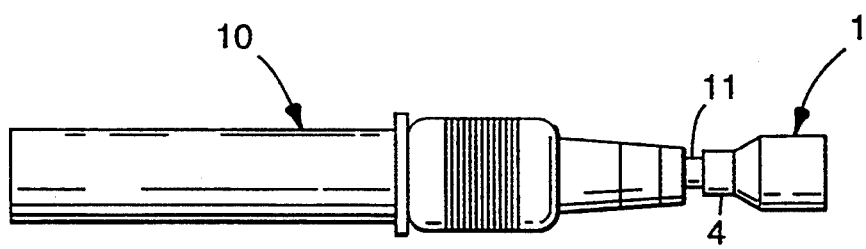
FIG.3
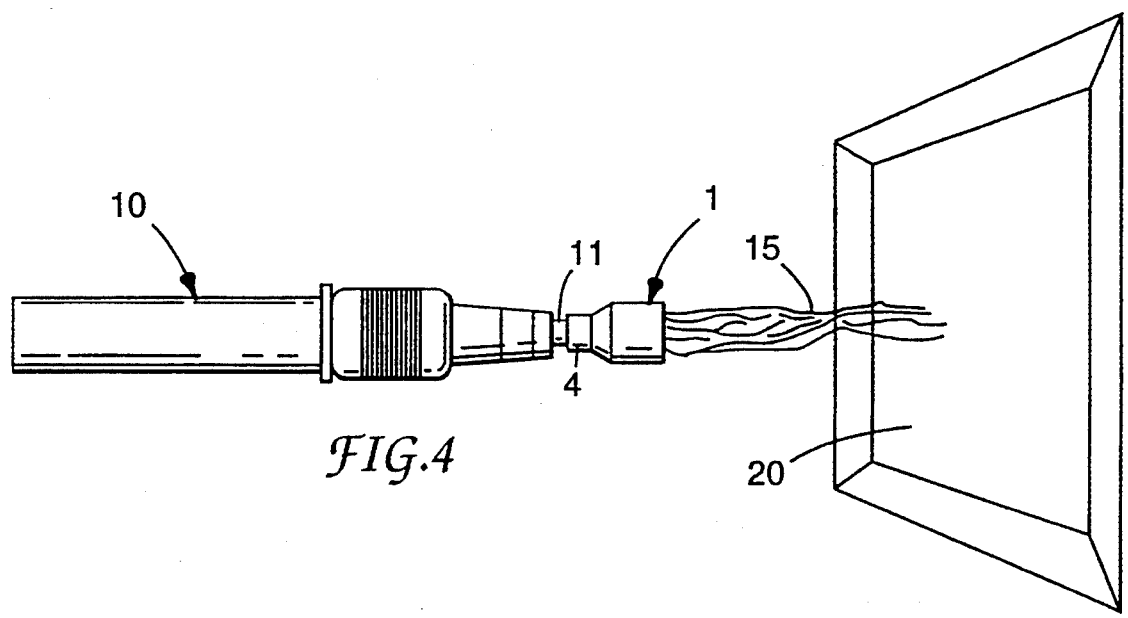
FIG.4

APPARATUS FOR CYANOACRYLATE FINGERPRINT DEVELOPING AND METHOD OF USE THEREFORE

RELATED APPLICATIONS

This application is a continuation in part of application Ser. No. 08/070,772 filed Jun. 3, 1993, now U.S. Pat. No. 5,348,759.

FIELD OF THE INVENTION

This invention relates to fingerprint developing devices and methods using cyanoacrylate and particularly to fingerprint developing devices and methods using a liquid form of cyanoacrylate that is vaporized and then propelled at some velocity toward the object to be tested.

BACKGROUND OF THE INVENTION

It is long known that cyanoacrylate, in vapor form, adheres to fingerprints. Once the vapor cures, the cyanoacrylate forms a white polymer substance that reveals to the fingerprint. This technique is known as developing a latent fingerprint. Although his process produces good results, the present technology for developing latent prints involves a time consuming process that must be performed in closed quarters. Current technology uses sheet packets of thick liquid cyanoacrylate. The cyanoacrylate is spread on sheets of material and then sealed. To use, the packet is opened by pulling the two sheets apart which then exposes the cyanoacrylate to the air. Typically, these sheets are placed in a closed vessel such as a large aquarium with the object to be examined. The cyanoacrylate vapors can then adhere to the object, developing any prints that might be on the object. This process can take up to six hours. One system calls for placing several packets throughout a room and then sealing the room for up to 24 hours to develop any prints that may be inside.

Examples of patents that use this technique can be found in U.S. Pat. Nos. 4,550,041; 4,729,229; 4,260,645, and 4,613,515. As noted above, these devices and methods all suffer from the same drawbacks: they are slow, taking up to several hours to complete the process, and must be used in a closed container.

It is also known that heat accelerates the vaporization of the cyanoacrylate. U.S. Pat. No. 4,719,119 discusses the drawbacks of using heat as it was taught in 1983. Essentially, the heat process uses a laboratory "hot plate" to warm the cyanoacrylate. In use, the opened pouch is placed on the hot plate within a closed container. As the heat is applied, vaporization accelerates. Notwithstanding the safety problems associated with this technique, it still requires that the test be conducted within a closed container such as an aquarium.

SUMMARY OF THE INVENTION

The present invention overcomes the problems associated with the prior art devices. The invention provides a fingerprint detection device which can be used in any location, including outdoors. The development of the latent prints often takes less than 30 seconds. The invention has a housing that holds a quantity of solid cyanoacrylate. Liquid cyanoacrylate is initially placed around the inner periphery of the housing and cured. One end of the housing is tapered to form a connecting tube. This connecting tube is then placed on the end of a small propane torch. The torch is used to vaporize the cyanoacrylate in the housing into a vapor, which is then propelled forward from the torch by the velocity of the torch exhaust gases. This vapor is then projected onto the test object, where latent prints will appear within seconds.

In a preferred embodiment, an empty housing is packed with a thermally stable fibrous or porous support material such as steel wool, woven wire or a porous ceramic. This support material is then impregnated with a liquid cyanoacrylate, which is then allowed to dry. The device is operated the same as before only this embodiment offers the additional benefit, that after the cyanoacrylate has been completely vaporized, the support material remains.

BRIEF DESCRIPTION OF THE DRAWING

FIG. 1 is a vertical-sectional view of the housing containing a fibrous or porous support material and cyanoacrylate ready for use and a fragmentary view of the tip of a torch, FIG. 2 is a vertical-sectional view of the housing containing steel wool impregnated with cyanoacrylate, ready for use, FIG. 3 is a side view of the housing as placed on the small torch, FIG. 4 is a detailed view of the device in use.

DETAILED DESCRIPTION OF THE INVENTION

Referring now to the drawing, the device has a cylindrical housing 1. The housing is open at the top 2. The bottom of the housing 3 can be tapered as shown. In the preferred embodiment, the taper is used to form a tapered base 3 of reduced internal diameter. This allows the housing 1 to be placed onto the exhaust port of a small commercially available propane torch, as discussed below. A connecting tube 4 is attached to the tapered base 3. This assembly can be constructed from one piece of metal.

In the preferred embodiment, the entire housing 1 is hollow with the open top and an open bottom formed by a solid wall. This permits a quantity of a thermally stable, preferably thermally conductive, fibrous or porous support material 5 to be located within the housing. Examples of such materials include steel wool, woven wire, and the like which will transfer heat. A quantity of a liquid cyanoacrylate 6 selected from the group consisting of monomeric cyanoacrylate esters, and polycyanoacrylate esters is then poured over the support material 5, and allowed to impregnate the support material and dry, or polymerize. The support material is preferably formed such that a cylindrical opening 7 is formed. This opening 7 conforms to the outside or inside diameter of the torch tip on ejector 11, (see FIGS. 2 and 3). Typically, the housing can be sized to match different sized torches by adjusting the internal diameter of tube 4.

The housing 1 is formed from cartridge brace which is shaped or by turning and drilling solid metal to form, preferably a hollow cylindrical housing. A quantity of thermally stable material is then packed in the open top to fill the top and tapered base. A quantity of liquid cyanoacrylate is then poured into the housing while turning the housing to impregnate the porous material and the cyanoacrylate is allowed to polymerize or cure.

In the preferred embodiment, a small propane torch 10, as shown in FIG. 3, is used to vaporize the cyanoacrylate 6 stored within the housing. The preferred torch is an ULTRATORCH ™ MODEL UT-50. These torches are available from the Master Appliance Corporation, 2420 18th Street, Racine, Wis. 53401. These torches provide sufficient heat to vaporize the cyanoacrylate. This size torch can be used indoors or outdoors.

In use, the torch 10 is lit. Then the housing 1 is placed over the lit torch ejector 11 at the connecting tube 4. The exhaust is then directed toward the object to be tested. FIG. 4 shows the device in use. As the cyanoacrylate 6 is vaporized, it is propelled forward toward the object being tested 20, developing any latent fingerprints thereon. This forward motion of the exhaust gas 15 focuses the cyanoacrylate vapor stream on the object and produces much faster developing times. This compares to the evaporative type developers, discussed above, that must operate in a closed environment and over long periods of time.

An alternative embodiment uses granulated cyanoacrylate 8 that is packed around the housing, with or without the use of the support material. When the granulated cyanoacrylate 8 is used up, the housing 1 can be discarded, and a new housing can be substituted, and the process can continue. It is possible to change housings by using pliers without shutting off the torch although this is not recommended.

The present disclosure should not be construed in any limited sense other than limited by the scope of the claims having regard to the teachings herein and the prior art being apparent with the preferred form the invention disclosed herein that reveals details of structure of a preferred form necessary for a better understanding of the invention and may be subject to change by skilled persons within the scope of the invention without departing from the concept thereof.

We claim:

1. A housing for developing latent fingerprints on objects using cyanoacrylate comprising:
a cylindrical housing having an open top and an open bottom and a solid wall, said housing containing a quantity of thermally stable, thermally conductive, porous support material, said support material being impregnated with liquid cyanoacrylate cured to a solid form in said support material and having an open area in its center extending the length of said material.

2. The housing according to claim 1 wherein said thermally stable support material comprises steel wool.

3. The housing according to claim 1 wherein said thermally stable support material comprises steel wool packed into the housing against the wall.

4. A device for developing latent fingerprints on objects using liquid cyanoacrylate comprising:
a) a removable cylindrical housing having an open top and an open bottom and a solid wall, said housing containing a quantity of thermally stable support material selected from the group consisting of porous and fibrous support material, said support material being impregnated with a liquid cyanoacrylate, and
b) heating means for producing sufficient temperature to sublimate the cyanoacrylate and having an exhaust gas with sufficient velocity that projects the sublimated cyanoacrylate from said housing in an outward direction, said heating means being removably connected to the open bottom of said housing such that said exhaust gases pass through said housing and exit therefrom through said open top.

5. A device according to claim 4 wherein said support material is a fibrous material packed into said housing against said wall such that said support material forms a cylinder within the cylindrical housing, said support material having an open cylindrical area in its center.

6. The device for developing latent fingerprints of claim 4 wherein said heating means comprises a portable blowtorch.

7. The method for making a housing device containing a quantity of cyanoacrylate adapted to be vaporized for developing latent fingerprints comprising the steps of
taking a hollow metal housing having a forward end and a bottom end, inserting a quantity of a thermally stable porous material into said housing, pouring a quantity of liquid cyanoacrylate into the housing to impregnate the thermally stable porous material, and allowing the liquid cyanoacrylate to polymerize.

8. A method of developing latent fingerprints on an object, using liquid cyanoacrylate comprising the steps of:
a) providing a housing, having a forward end, a bottom end and a solid wall, and a quantity of solid cyanoacrylate within said housing,
b) attaching the bottom end of said housing to the exhaust port of a propane torch,
c) lighting said torch, thereby producing a relatively high temperature exhaust gas having a forward velocity,
d) projecting said exhaust gas through said housing and cyanoacrylate, causing said cyanoacrylate to sublimate into a vapor,
e) positioning said exhaust gas and said cyanoacrylate vapor being discharged from said forward end onto a said object for testing
whereby the cyanoacrylate deposits onto said object to develop any said latent fingerprints.

9. The method of developing latent fingerprints of claim 8 wherein said housing has a porous support material positioned within said housing against said wall, which support material is impregnated initially by liquid cyanoacrylate which is allowed to cure.

10. The method according to claim 9 wherein said support material is selected from the group consisting of steel wool, wire or ceramic.

11. The method of developing latent fingerprints according to claim 9 wherein the support material is steel wool.

12. The method of developing latent fingerprints according to claim 8 wherein said heating device is a propane torch.

13. The method of developing latent fingerprints according to claim 9 wherein said heating device is a propane torch.

* * * * *